United States Patent [19]

Bonzel

[11] Patent Number: 5,232,445
[45] Date of Patent: Aug. 3, 1993

[54] DILATATION CATHETER

[76] Inventor: Tassilo Bonzel, Neumattenstrasse 27, D-7800, Freiburg, Fed. Rep. of Germany

[21] Appl. No.: 773,738

[22] Filed: Oct. 9, 1991

Related U.S. Application Data

[63] Continuation of Ser. No. 634,931, Dec. 27, 1990, abandoned, which is a continuation of Ser. No. 203,844, Jun. 8, 1988, abandoned, which is a continuation of Ser. No. 893,558, Jul. 14, 1986, Pat. No. 4,762,129.

[51] Int. Cl.$^5$ ............................................. A61M 25/00
[52] U.S. Cl. ........................................ 604/96; 606/194
[58] Field of Search ................................ 606/191-195; 604/96-103

[56] References Cited

U.S. PATENT DOCUMENTS

| | | | |
|---|---|---|---|
| 1,060,665 | 5/1913 | Bell | 604/281 |
| 2,383,968 | 9/1945 | DeLuca et al. | |
| 2,657,691 | 11/1953 | Nordstrom, Jr. | |
| 2,687,131 | 8/1954 | Raiche | |
| 2,883,986 | 4/1959 | DeLuca et al. | 128/207.15 |
| 2,936,760 | 5/1960 | Gants | |
| 3,225,762 | 12/1965 | Guttman | |
| 3,435,826 | 4/1969 | Fogarty et al. | |
| 3,467,101 | 9/1969 | Fogarty et al. | |
| 3,731,692 | 5/1973 | Goodyear | 128/207.15 |
| 3,757,768 | 9/1973 | Kline | |
| 3,766,924 | 10/1973 | Pidgeon | |
| 3,769,981 | 11/1973 | McWhorter | 604/96 |
| 3,882,852 | 5/1975 | Sinnreich | 128/4 |
| 4,195,637 | 4/1980 | Gruntzig et al. | |
| 4,198,981 | 4/1980 | Sinnreich | 128/344 |
| 4,236,521 | 12/1980 | Lauterjung | |
| 4,244,362 | 1/1981 | Anderson | 128/200.26 |
| 4,271,839 | 6/1981 | Fogarty et al. | |
| 4,289,128 | 9/1981 | Rusch | 128/204.25 |
| 4,299,226 | 11/1981 | Banka | |
| 4,323,071 | 4/1982 | Simpson et al. | |
| 4,367,747 | 1/1983 | Witzel | 128/344 |
| 4,413,989 | 11/1983 | Schjeldahl et al. | 604/96 |
| 4,439,186 | 3/1984 | Kuhl | 604/99 |
| 4,468,224 | 8/1984 | Enzmann et al. | |
| 4,479,497 | 10/1984 | Fogarty et al. | |
| 4,490,421 | 12/1984 | Levy | |
| 4,526,175 | 7/1985 | Chin et al. | |
| 4,545,390 | 10/1985 | Leary | 128/772 |
| 4,554,929 | 11/1985 | Samson et al. | |
| 4,571,240 | 2/1986 | Samson et al. | |
| 4,573,966 | 3/1986 | Weikl | |
| 4,582,181 | 4/1986 | Samson | 128/344 |
| 4,585,000 | 4/1986 | Hershenson | 128/345 |
| 4,597,755 | 7/1986 | Samson et al. | |
| 4,610,662 | 9/1986 | Weikl et al. | |
| 4,616,648 | 10/1986 | Simpson | 128/303 R |
| 4,630,609 | 12/1986 | Chin | |
| 4,637,396 | 1/1987 | Cook | |
| 4,662,368 | 5/1987 | Hussein et al. | 128/303.1 |
| 4,684,363 | 8/1987 | Ari et al. | |
| 4,702,252 | 10/1987 | Brooks et al. | |
| 4,824,435 | 4/1989 | Giesy et al. | |

FOREIGN PATENT DOCUMENTS 867144 12/1952 Fed. Rep. of Germany .
2828447 9/1979 Fed. Rep. of Germany .

(List continued on next page.)

OTHER PUBLICATIONS

Nordenstrom, B.: "New Instruments For Catheterization and Angiocardiography", *Acta Radiology*, vol. 85, pp. 256-259 (Jul.-Dec. 1965).

Nordenstrom, B.: "Balloon Catheters For Percutaneous Insertion Into The Vascular System", *Acta Radiology*, vol. 57, Nov. 1962, pp. 411-416.

(List continued on next page.)

Primary Examiner—C. Fred Rosenbaum
Assistant Examiner—William Lewis
Attorney, Agent, or Firm—Pennie & Edmonds

[57] ABSTRACT

A dilatation catheter, in particular for expanding constrictions in coronary vessels, includes a balloon (2) capable of being enlarged by injecting a fluid through a tube (3). The tube (3) is arranged laterally offset from a segment of flexible tubing (7) by which a passage (8) for a guide wire (1) is formed in the balloon (2).

2 Claims, 1 Drawing Sheet

FOREIGN PATENT DOCUMENTS

| | | |
|---|---|---|
| 2918282 | 11/1980 | Fed. Rep. of Germany . |
| 3028089 | 2/1981 | Fed. Rep. of Germany . |
| 2934628 | 3/1981 | Fed. Rep. of Germany . |
| 3107392 | 9/1982 | Fed. Rep. of Germany . |
| 329354 | 7/1903 | France . |
| 591963 | 7/1925 | France . |
| 340425 | 6/1972 | U.S.S.R. . |
| 627828 | 10/1978 | U.S.S.R. . |
| 1251914 | 8/1986 | U.S.S.R. ............................. 128/344 |
| 1566308 | 4/1980 | United Kingdom . |
| 2180454 | 4/1987 | United Kingdom . |

OTHER PUBLICATIONS

Nordenstrom, B.: "Temporary Unilateral Occlusion of the Pulmonary Artery: A Method of Roetgen Examination of The Pulmonary Vessels:", *Acta Radiology Suppl.* No. 108, 1954, pp. 1–30.

Fogarty et al., "Adjunctive Intraoperative Arterial Dilation", Arch. Surg., 116:1391–1398 (Nov. 1981).

Hawkins et al., "Minicatheter and Deflector Technique For Renal Angioplasty", Radiology, 145:837–838 (Dec. 1982).

Simpson et al., "A New Catheter System For Coronary Angioplasty", Am. Jour. Cardiology, 49:1216–1222 (Apr. 1982).

Dotter, C. T., "Transluminal Angioplasty: A Long View", Radiology, 135:561–564 (Jun. 1980).

Zeitler et al., "Results of Percutaneous Transluminal Angioplasty", Radiology, 146:57–60 (Jan. 1983).

Fogarty et al., "A Method For Extraction of Arterial Emboli and Thrombi", Surgery, Gynecology & Obstetrics, Feb. 1963 pp. 241–243.

Abele, "Balloon Catheters and Transluminal Dilatation: Technical Considerations", AJR, vol. 135, pp. 901–906 (Nov. 1980).

Annual Review of Medicine: Selected Topics in the Clinical Sciences, Kennedy & Stewart, vol. 35, pp. 514–522 (1984).

Castaneda-Zuniga, *Transluminal Angioplasty*, pp. 1–27 (1983).

*The Condensed Chemical Dictionary*, by Gessner G. Hawley, p. 836 (1981).

Cumberland, D. C., "Percutaneous Transluminal Angioplasty: A Review", Clinical Radiology, vol. 34, pp. 25–38 (1983).

Earlam et al., "Benign Oesophageal Strictures: Historial and Technical Aspects of Dilatation", *the British Journal of Surgery*, vol. 68, No. 12 (Dec. 1981).

Fogarty Arterial Embolectomy Cather Instructions, American Edwards Laboratories, pp. 1–4 (Aug. 1984).

Fogarty et al., "Combined Thrombectomy and Dilation for the Treatment of Acute Lower Extremity Arterial Thrombosis", *J. Vasc. Surg.*, vol. 10, No. 5, pp. 530–534 (Nov. 1989).

Fogarty et al., "Intraoperative Coronary Artery Balloon Catheter Dilatation", *Am. Heart J., vol. 107, No. 9, pp. 845–851 (Apr. 1984)*.

Fogarty, "Management of Arterial Emboli", Symposium on Peripheral Vascular Surgery, *Surgical Clinics of North America*, vol. 59, No. 4, pp. 747–753 (Aug. 79).

Fogarty et al., "Peroperative Transluminal Angioplasty", pp. 313–321.

Friedberg, "Dilatation of Esophagael Strictures in Children, Using a Fogarty Balloon Catheter", presented at 33rd Annual Meeting of Canadian Othotaryngological Society (Jun. 1979).

Gruntzig et al., "Current Status of Dilatation Catheters and Guiding Systems", *Am. J. Cardiol.*, vol. 53, pp. 92C–93C (Jun. 1984).

Gruntzig, "PTCA Technique With A Double Lumen Dilatation Catheter", published in *The Proceeding of the Workshop on Percutaneous Transluminal Coronary Angioplasty, NIH Publication No. 80–2030, pp. 123–133 (Mar. 1980)*.

Gruntzig, "Transluminal Dilatation of Coronary Stenosis", *Lancet* 1:263 (1978).

Kaltenbach, "The Long Wire Technique-A New Technique for Steerable Balloon Catheter Dilatation of Conorary Artery Stenosis", *European Heart J.*, vol. 5, pp. 1004–1009 (Dec. 1984).

Kaltenbach, "Neue Technik Zur Steuerbaren Ballondilatation Von Kranzgefassverengungen", Z. Kardiol, 73:669–673 (Nov. 1984).

Kinney et al., "Transluminal Angioplasty: A Mechanical-Pathophysiological Correlation of its Physical Mechanisms", Radiology, vol. 153, pp. 85–89 (Oct. 1984).

Kugimiya et al., "The Use of a Fogarty Balloon Catheter for Dilatation of Postoperative Esophagael Stricture", *Kyobu Geka*, vol. 30, No. 5, pp. 419–422 (1977).

McAuley et al., "Advances in Guidewire Technology", *Am. J. Cardiol.*, 53:94C–96C (1984).

(List continued on next page.)

OTHER PUBLICATIONS

Moersch, "Cardiospasm:Its Diagnosis and Treatment", pp. 232–238 (1932).

Nordenstrom, "Percutaneous Balloon–Occlusion of the Aorta", *Acta Radiol.*, vol. 4, pp. 356–374 (1966).

Portsmann, "Ein Neuer Korsett–Ballonkatheter Zur Transluminalen Rekanalisation Nach Dotter Unter Besonderer Berucksichigung Von Obliterationen An Den Beckenarterien", *Radio. Diaga* (Berl.), vol. 14, pp. 239–244 (1973).

Seldinger, "Catheter Replacement of the Needle in Percutaneous Arteriography", *Acta Radiol.*, vol. 39, pp. 368–376 (1952).

Taber's Cyclopedic Dictionary, p. 768.

Waltman et al., "Transluminal Angioplasty: General Rules and Basic Considerations", *Interventional Radiology* pp. 253–272 (1982).

21 C.F.R. §§870.1–870.1650 (1980).

Kifa Sales Literature, "Catheterization Equipment", 1968.

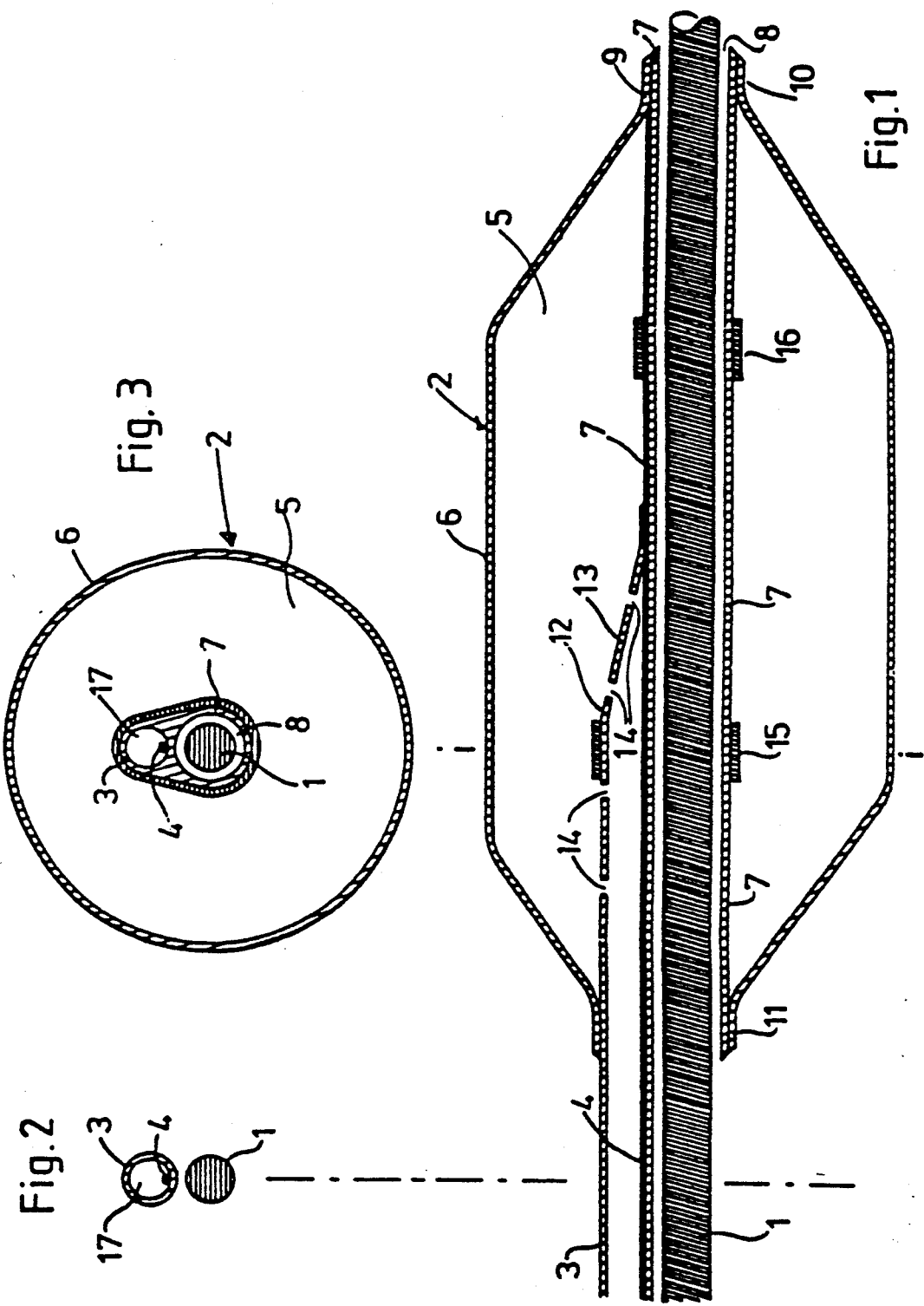

DILATATION CATHETER

This is a continuation of application Ser. No. 07/634,931 filed Dec. 27, 1990, now abandoned, which is a continuation of 07/203,844, filed Jun. 8, 1988, now abandoned, which is a continuation of 06/893,558, filed Jul. 14, 1986, now U.S. Pat. No. 4,762,129.

BACKGROUND OF THE INVENTION

The invention relates to a dilatation catheter having a tube the operative end of which opens into an expandable balloon and a segment of flexible tubing traversing the balloon, sealingly connected to the distal end of the balloon, and capable of being threaded by a guide wire.

Such a dilatation catheter is described in The American Journal of Cardiology, Vol. 49, Apr. 1, 1982, pages 1216 to 1222, and is employed to enlarge constrictions in vessels and body cavities, in particular coronary arteries. At the tip of such a dilatation catheter, an inflatable balloon is disposed, capable of being filled or emptied by way of a lumen inside the catheter.

In the known dilatation catheter, a tube is provided that passes over into a balloon at its anterior end. Through the interior of the balloon and the tube, in the known dilatation catheter, a flexible tube extends, projecting beyond the anterior end of the balloon and sealingly connected to the anterior end of the balloon. Through the inside of the flexible tube, a guide wire is passed, capable of being displaced relative to the balloon during the operation, so that the dilatation catheter can be advanced or retracted along the guide wire. When replacing a dilatation catheter applied with the aid of a guide catheter, it is necessary that the guide wire protrude from the patient's body by a length greater than the length of the dilatation catheter with tube. For this reason, manipulation of the known dilatation catheter is difficult, especially since the forces of friction between the guide wire and the flexible tubing passing all the way through the balloon and the tube are great.

SUMMARY OF THE INVENTION

Departing from this prior art, the object of the invention is to create a dilatation catheter that can be passed easily along a guide wire and simply and easily replaced by another dilatation catheter.

This object is accomplished, according to the invention, in that the proximal end of the balloon is likewise sealingly attached to the length of flexible tubing, and in that the tube opens into the interior of the balloon laterally displaced from the segment of tubing.

Since the segment of tubing coming into contact with the surface of the guide wire is only about as long as the balloon and the tube no longer encloses the guide wire and the guide tubing enclosing it, manipulation of the dilatation catheter is facilitated. Control is improved because of the absence of frictional forces in a long segment of guide tubing. Furthermore, owing to the comparative shortness of the length of tubing, the guide wire need no longer protrude from the patient's body by about the same length as the length of the dilatation catheter.

Suitable embodiments and refinements of the invention are described elsewhere in the present application.

DETAILED DESCRIPTION OF THE INVENTION

The invention will now be illustrated with reference to the embodiment represented in the drawing by way of example. In the drawing, FIG. 1 shows the anterior portion of the dilatation catheter according to the invention, with tube opening into the balloon, FIG. 2 shows a cross section of a dilatation catheter in the region of the tube, passing alongside the guide wire, and FIG. 3 shows a cross section of the dilatation catheter in the region of a gold marker in the balloon.

In FIG. 1, the anterior portion of a dilatation catheter is represented, to be advanced with the aid of a guide catheter not shown in the drawing, having a diameter of some millimeters and a length of about one meter, for example from a patient's right groin throughout the length of the artery to the aorta and the coronary arteries. Through the guide catheter not shown in the drawing, first a guide wire 1 is advanced into the corresponding coronary. A segment of the guide wire 1, which is about 1 m in length, may be seen in FIG. 1. The guide wire 1 serves as instrumentation track to guide the dilatation catheter.

The dilatation catheter has a balloon tube and a tube 3, shown cut away in FIG. 1 and likewise on the order of 1 m in length.

FIG. 2 shows a section of the guide wire 1 and tube 3. The tube 3 serves firstly to transmit thrusts and tensions for pushing the balloon 2 to and fro and rotating it on the guide wire 1. For this reason, it is desirable for the tube 3 to be reinforced by a stabilizing wire 4 in the manner shown in FIGS. 1 to 3. Besides its function of transmitting forces, the tube 3 serves for injection of fluids into the interior 5 of the balloon 2 and for aspiration of fluids when the diameter of the balloon is to be decreased.

As may be seen in FIG. 1, the balloon consists of an envelope 6 and a length of flexible tubing 7, so that the balloon 2 has a passage 8 sealed off from the interior 5 of the balloon. The balloon passage 8 enables the balloon 2 to be thrust onto the guide wire 1 and thereby guided along the guide wire 1.

In FIG. 3, the substantially annular cross section of the balloon 2 is seen, together with the balloon passage 8 through which the guide wire 1 extends. For good transmission of the forces exerted upon the tube 3 to the balloon 2, the stabilizing wire 4 extends into the neighborhood of the distal end 9 of the balloon 2.

As is clearly seen in FIG. 1, at the distal end 9 of the balloon 2 the envelope 6 takes the form of a length of flexible tubing 10, tightly connected to the distal end of the segment of tubing 7. Similarly, the envelope 6 terminates at the proximal end in a segment of tubing 11, sealingly connected firstly to the proximal end of segment 7 and secondly to the tube 3.

The operative end 12 of tube 3, pointing to the right in FIG. 1, terminates in a taper 13 fixed to the tubing 7. Both in the taper 13 and elsewhere at the operative end 12, radial openings 14 are provided in the tube 3, whereby fluid injected into the tube 3 can pass from the tube 3 into the interior 5 of the balloon 2.

In FIGS. 1 and 3, gold stripes 15 and 16 are additionally represented, serving to mark the location of the dilatation catheter in X-ray views.

In FIG. 3, we see a cross section of the balloon 2 in the region of the gold strip 15. The tube 3 with its inner lumen 17 and the segment of tubing 7 with balloon passage 8 are made in one piece in the region shown in FIG. 3, so that the gold stripe 15 assumes a substantially oval form rather than that of a figure-eight.

The guide wire 1 may have a central lumen, not shown in the drawing, for pressure measurement or to contain a contrast medium. To minimize frictional resistance between the interior of the balloon passage 8 and the surface of the guide wire 1, the inside of the tubing segment 7, reinforced by the stabilizing wire 4, and/or the top of the guide wire 1 may be provided with a lubricant coating.

For dilatation of coronary vessels, first the guide wire 1 is introduced through the guide catheter into the proper coronary artery. The guide wire 1 lies freely in the guide catheter and so may be conveniently rotated and controlled. For anatomical orientation, adequate additional doses of contrast medium may be supplied. When the guide wire 1 has passed the constriction in the coronary artery, the tip of the guide wire 1 remains on the far side of the stenosis in the coronary vessel. At this point, and not until, the dilatation catheter according to the invention is thrust onto the guide wire 1 outside the body and advanced through the guide catheter along the track formed by the guide wire 1 into the coronary artery and under the constriction. If the balloon 2 is to be replaced during the operation by a balloon 2 of larger size, it is a simple matter to retract the dilatation catheter according to the invention, leaving the anterior end of the guide wire 1 in the coronary vessel and permitting secure advancement of the replacement balloon with no need to overcome much friction or to relocate the stenosis a second time. If deficient stability of the result of dilatation is suspected, the guide wire 1 may even be left in place for several hours, with a view to renewed dilatation at a later time. The distal end 9 of the dilatation catheter is flattened in the manner described above for better insertability into vascular constrictions.

The invention permits the provision of balloons of various lengths, widths and wall thicknesses to accommodate various pressures, and they may be interchanged with ease. Depending on medical requirements, the dilatation catheters are equipped with tubes 3 of varying weight and flexibility, admitting of differential advance. For larger dilatation catheters, an additional inner lumen, not shown in the drawing, is provided, its anterior end extending to the distal end 9 of the balloon 2 and communicating with the interior of the vessel inside the patient's body. In this way, pressure measurements and injections of contrast medium may be performed. The guide wires 1 of a complete instrumentarium are likewise of different weights and flexibilities. The guide wires 1 have soft, flexible tips, which may be shorter or longer, as well as straight or bowed. If no additional inner lumen is provided in the balloon, a central lumen as above mentioned may be provided in the guide wires for pressure measurements and injections of contrast medium.

I claim:

1. A coronary angioplasty dilatation catheter comprising
    an expandable balloon having distal and proximal ends;
    a first, relatively long, elongated hollow tube having distal and proximal ends and opening adjacent its distal end into the interior of the expandable balloon, the first tube being sealingly connected to the proximal end of the balloon;
    a second, relatively short, elongated hollow tube integral with said first tube, having distal and proximal ends, and adapted to receive a guide wire in a sliding fit, the second tube traversing the interior of the expandable balloon from the distal end to the proximal end of the balloon and being sealingly connected to the distal end of the balloon, and the second tube terminating at its proximal end substantially distally of the proximal end of the first tube in an aperture open to the exterior of the catheter; and
    means for imparting sufficient stiffness to said first tube that the second tube and expandable balloon can readily be advanced or withdrawn together in use along the guide wire by exerting a pushing or pulling force upon the first tube, and
    wherein the first tube is reinforced by means of a longitudinally-extending stabilizing wire, and
    wherein the first tube is laterally displaced from the second tube, and the stabilizing wire extends in the interior of the expandable balloon beyond the distal end of the first tube and along the outer surface of the second tube into the vicinity of the distal end of the expandable balloon,
with the dimensions of said dilatation catheter being such that it can be advanced in the vascular system of a human patient over the guide wire, with said expandable balloon in an unexpanded condition and the guide wire in a sliding fit within said second tube, until the expandable balloon is located within a coronary artery.

2. A coronary angioplasty dilatation catheter comprising
    an expandable balloon having distal and proximal ends;
    a first, relatively long, elongated hollow tube having distal and proximal ends and opening adjacent its distal end into the interior of the expandable balloon, the first tube being sealingly connected to the proximal end of the balloon;
    a second, relatively short, elongated hollow tube integral with said first tube, having distal and proximal ends, and adapted to receive a guide wire in a sliding fit, the second tube traversing the interior of the expandable balloon from the distal end to the proximal end of the balloon and being sealingly connected to the distal end of the balloon, and the second tube terminating at its proximal end substantially distally of the proximal end of the first tube in an aperture open to the exterior of the catheter; and
    means for imparting sufficient stiffness to said first tube that the second tube and expandable balloon can readily be advanced or withdrawn together in use along the guide wire by exerting a pushing or pulling force upon the first tube; and
    wherein the wall of the first tube is provided with a plurality of lateral openings to provide fluid communication with the interior of the expandable balloon and;
    wherein said first tube terminates in a tapered portion at its distal end, and said lateral openings are provided in said tapered portion;
with the dimensions of said dilatation catheter being such that it can be advanced in the vascular system of a human patient over the guide wire, with said expandable balloon in an unexpanded condition and the guide wire in a sliding fit within said second tube, until the expandable balloon is located within a coronary artery.

* * * * *